United States Patent
Ng et al.

(10) Patent No.: US 12,268,485 B2
(45) Date of Patent: Apr. 8, 2025

(54) PHOTOPLETHYSMOGRAM CIRCUIT, BIOLOGICAL CHARACTERISTICS DETECTION DEVICE AND BIOLOGICAL CHARACTERISTICS DETECTION METHOD

(71) Applicant: SHENZHEN GOODIX TECHNOLOGY CO., LTD., Guangdong (CN)

(72) Inventors: Si Herng Ng, Guangdong (CN); Wen-Chi Wang, Guangdong (CN)

(73) Assignee: SHENZHEN GOODIX TECHNOLOGY CO., LTD., Guangdong (CN)

( * ) Notice: Subject to any disclaimer, the term of this patent is extended or adjusted under 35 U.S.C. 154(b) by 1053 days.

(21) Appl. No.: 17/122,983

(22) Filed: Dec. 15, 2020

(65) Prior Publication Data
US 2021/0161413 A1    Jun. 3, 2021

Related U.S. Application Data

(63) Continuation of application No. PCT/CN2019/121910, filed on Nov. 29, 2019.

(51) Int. Cl.
  *A61B 5/024* (2006.01)
  *A61B 5/00* (2006.01)
  *A61B 5/307* (2021.01)

(52) U.S. Cl.
  CPC .......... *A61B 5/02416* (2013.01); *A61B 5/307* (2021.01); *A61B 5/6802* (2013.01)

(58) Field of Classification Search
  CPC .............. A61B 5/0059; A61B 5/02108; A61B 5/02416; A61B 5/02427; A61B 5/0261;
  (Continued)

(56) References Cited

U.S. PATENT DOCUMENTS

2008/0242958 A1\* 10/2008 Al-Ali ................. A61B 5/6838
                                                                600/323
2010/0069780 A1    3/2010 Schuette et al.
(Continued)

FOREIGN PATENT DOCUMENTS

CN    105223137 A    1/2016
CN    109069038 A    12/2018
(Continued)

OTHER PUBLICATIONS

Abstract of CN105223137A.
(Continued)

*Primary Examiner* — Boniface N Nganga
(74) *Attorney, Agent, or Firm* — WPAT, P.C., INTELLECTUAL PROPERTY ATTORNEYS; Anthony King

(57) ABSTRACT

The present application discloses a PPG circuit, a biological characteristics detection device and a biological characteristics detection method. The PPG circuit is configured to control a light source and N photoelectric converters to sense biological characteristics of an object under test; the PPG circuit includes: a transmitting channel, K receiving channels, wherein the N photoelectric converters are divided into K sets of photoelectric converter sets, and the K receiving channels respectively correspond to K sets of photoelectric converter sets; and a controller, configured to control the PPG circuit to operate in a partial sampling phase or an full sampling phase, so as to generates J or K biological characteristics sampling results during each of the pulse repetition cycles.

12 Claims, 3 Drawing Sheets

(58) Field of Classification Search
CPC ... A61B 5/14552; A61B 5/307; A61B 5/6802; A61B 5/7225; A61B 2560/0209; A61B 2560/0233; G01D 5/14; G01D 5/34; G01N 21/17; G01N 2021/174
See application file for complete search history.

(56) References Cited

U.S. PATENT DOCUMENTS

| | | | |
|---|---|---|---|
| 2011/0201946 A1* | 8/2011 | Turcott | A61B 5/1455 600/300 |
| 2013/0261415 A1 | 10/2013 | Ashe et al. | |
| 2016/0198964 A1* | 7/2016 | Lee | A61B 5/6898 600/479 |
| 2017/0347902 A1* | 12/2017 | Van Gool | A61B 5/02427 |
| 2018/0000363 A1 | 1/2018 | Pekonen et al. | |
| 2018/0353075 A1* | 12/2018 | Duval | A61B 5/6823 |
| 2019/0090766 A1 | 3/2019 | Block et al. | |
| 2019/0290146 A1 | 9/2019 | Schipper et al. | |

FOREIGN PATENT DOCUMENTS

| | | |
|---|---|---|
| CN | 109788919 A | 5/2019 |
| CN | 110477895 A | 11/2019 |
| JP | 2018502623 A | 2/2018 |
| KR | 20180000159 A | 1/2018 |
| TW | 201116254 A1 | 5/2011 |

OTHER PUBLICATIONS

Abstract of CN109069038A.
Abstract of CN109788919A.
Abstract of CN110477895A.
Abstract of TW201116254A.
Application No. PCT/CN2019/121910 as filed.
PCT/ISA/Form 202 from PCT/CN2019/121910.
PCT/ISA/Form 210 from PCT/CN2019/121910.
PCT/ISA/Form 220 from PCT/CN2019/121910.
PCT/ISA/Form 237 from PCT/CN2019/121910.
PCT/RO/Form 105 from PCT/CN2019/121910.
Request from PCT/CN2019/121910.
English abstract translation of JP2018502623A.
English abstract translation of KR20180000159A.

\* cited by examiner

30

PHOTOPLETHYSMOGRAM CIRCUIT, BIOLOGICAL CHARACTERISTICS DETECTION DEVICE AND BIOLOGICAL CHARACTERISTICS DETECTION METHOD

CROSS REFERENCE TO RELATED APPLICATIONS

The present disclosure is a continuation of international application No. PCT/CN2019/121910, filed on Nov. 29, 2019, which is hereby incorporated by reference in its entirety.

TECHNICAL FIELD

The present application relates to a photoplethysmogram (PPG) circuit; in particular, to a PPG circuit, a biological characteristics detection device and a biological characteristics detection method capable of using multiple receiving channels to reduce power consumption and improve accuracy.

BACKGROUND

Biological characteristics detection devices have promising applications in detecting biological characteristics, such as human blood pressure, blood flow, blood oxygen, cerebral oxygen, muscle oxygen, blood glucose, microcirculatory peripheral vascular pulse rate, respiratory rate and respiratory volume. The PPG front-end processing module is an important component of these wearable non-invasive detection devices. The accuracy of biological characteristics detection using a biological characteristics detection device is affected by the fact that the phototransducer of the biological characteristics detection device may not be positioned in the exact location of the blood vessels during the measurement or the biological characteristics detection device may be displaced relative to the body during the test. Therefore, it is necessary to address the above-mentioned issues.

SUMMARY OF THE INVENTION

One purpose of the present application is to disclose a PPG circuit, a biological characteristics detection device and a biological characteristics detection method to address the above-mentioned issues.

One embodiment of the present application discloses a PPG circuit, which configured to control a light source and N photoelectric converters to sense biological characteristics of an object under test, wherein N is an integer greater than 1, and the PPG circuit includes: a transmitting channel, configured to control the light source to perform light emitting operations during pulse repetition cycles; K receiving channels, wherein K is an integer greater than 1, and the N photoelectric converters are divided into K sets of photoelectric converter sets, the K receiving channels respectively correspond to the K sets of photoelectric converter sets; and a controller, configured to control the PPG circuit to operates in a partial sampling phase or a full sampling phase, when the controller controls the PPG circuit to operate in the partial sampling phase, the controller activates J receiving channels of the K receiving channels as current receiving channels and activates J sets of photoelectric converter sets of the K sets of photoelectric converter sets corresponding to the J receiving channels to sense received light for performing the sampling operation, so as to generate J biological characteristics sampling results during each of the pulse repetition cycles, wherein J is smaller than K; and when the controller controls the PPG circuit to operate in the full sampling phase, the controller activates all receiving channels of the K receiving channels and activates all of the K sets of photoelectric converter sets to sense the received light for performing the sampling operation, so as to generate K biological characteristics sampling results during each of the pulse repetition cycles, and from the K receiving channels, re-select J receiving channels as the current receiving channels to be activated during the next partial sampling phase according to the K biological characteristics sampling results generated during each of the pulse repetition cycles of the full sampling phases.

Another embodiment of the present application discloses a biological characteristics detection device, including: the PPG circuit; the photoelectric converter; and the light source.

Another embodiment of the present application discloses a biological characteristics detection method, configured to control a light source and N photoelectric converters to sense biological characteristics of an object under test, wherein N is an integer greater than 1, the N photoelectric converters are divided into K sets of photoelectric converter sets, and the biological characteristics detection method includes: controlling the light source to perform only one light emitting operation during each of the pulse repetition cycles; during a partial sampling phase, only activating J sets of photoelectric converter sets of the K sets of photoelectric converter sets to simultaneously sense received light for performing sampling operation, and generating J biological characteristics sampling results via the activated J sets of photoelectric converter sets during each of the pulse repetition cycles, wherein J is smaller than K; and during the full sampling phase, activating all of the K sets of photoelectric converter sets to simultaneously sense the received light for performing the sampling operation, so as to generate K biological characteristics sampling results during each of the pulse repetition cycles, and from the K receiving channels, re-selecting J receiving channels as the current receiving channels to be activated during the next partial sampling phase according to the K biological characteristics sampling results generated during said each of the pulse repetition cycles of the full sampling phases.

The PPG circuit, biological characteristics detection device and biological characteristics detection method of the present application utilize multiple receiving channels to reduce the power consumption and increase the accuracy.

DETAILED DESCRIPTION

When measuring pulse cycle or cardiac blood oxygenation using the photoplethysmogram (PPG) technique, light is irradiated onto the skin to detect changes in the volume of blood perfusion to the dermis and subcutaneous tissue. As the volume of perfused blood changes, the amount of light absorbed also changes, and a subcutaneous blood plethysmogram can be obtained from the measured intensity of reflected light to reflect the heart rate and cardiac oxygen status. Biological characteristics detection devices typically use multiple photoconverters corresponding to multiple locations, and sample by using multiple photoconverters in turn during each pulse repetition cycle $T_{PF}$, or sample by using all photoconverters simultaneously which are connected in parallel so as to collect subcutaneous blood plethysmograms of different locations at one time during each pulse repetition cycle $T_{PF}$.

With respect to the method that photoelectric converters are used for sampling in turns, one has to drive the light source to emit light each time when the photoelectric converters perform the sampling process; that is, during each pulse repetition cycle, the light source has to be driven multiple times to sample the multiple photoelectric converters in turns, which leads to significant increase in the power consumption. With respect to the method that multiple photoelectric converters are connected in parallel, if only one or a few of the multiple photoelectric converters contain the valid information, such approach would greatly increase the requirement of the receiving channel to a dynamic range specification, thereby increasing the power consumption of the receiving channel of the biological characteristics detection device. Moreover, connecting multiple photoelectric converters in parallel would greatly increase the parasitic capacitance effect, causing more difficulties in the stability design of the current-to-voltage converter of the receiving channel of the biological characteristics detection device and an increase in the noise amplification effect thereof, and the power consumption of the current-to-voltage converter will increase significantly if it is intended to achieve the noise level and circuit stability of a single photoelectric converter.

The present application uses multiple receiving channels in a biological characteristics detection device to reduce the power consumption and increase the accuracy of such device.

Figure 1:
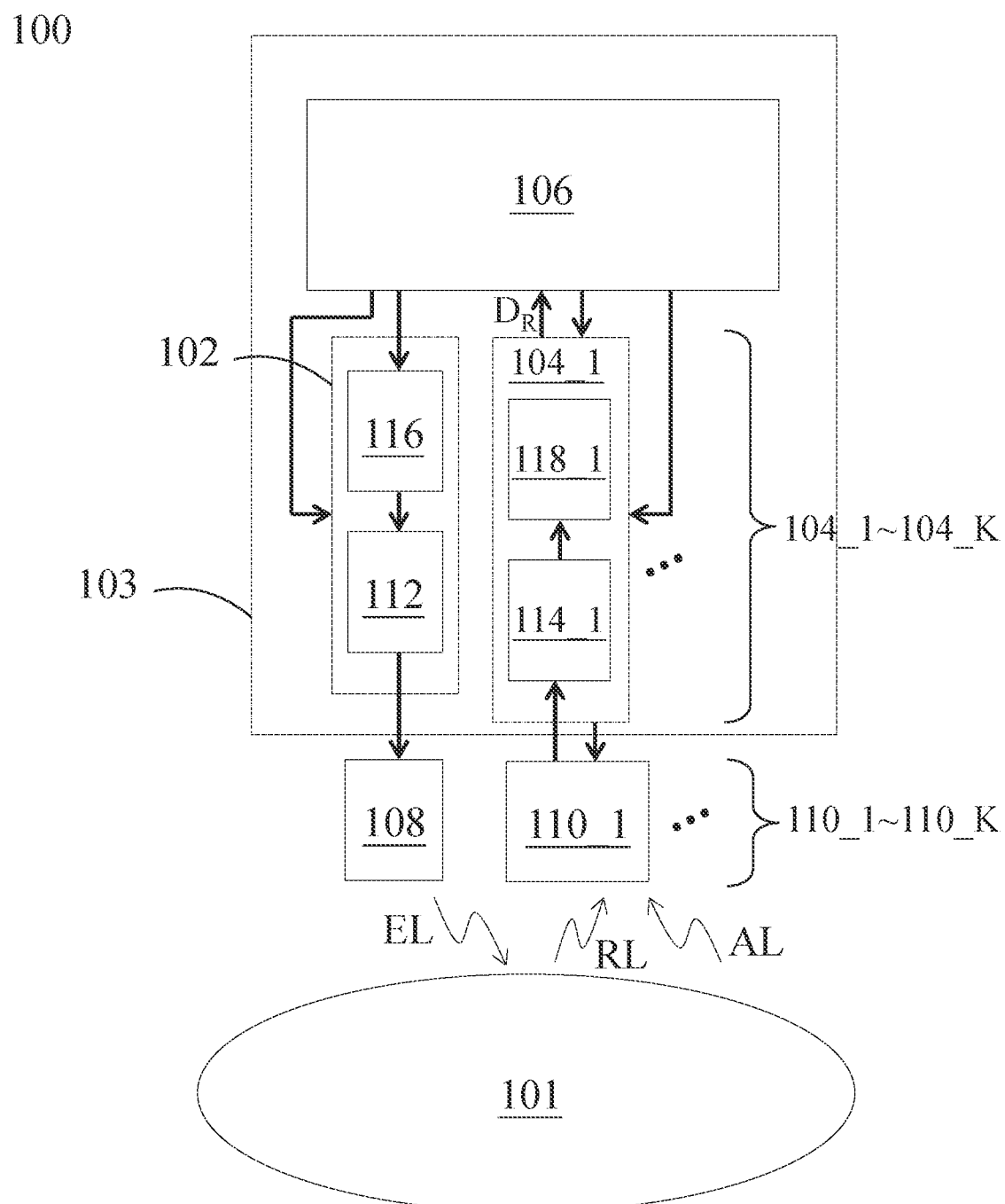
FIG. 1 is a functional block diagram of a biological characteristics detection device according to embodiments of the present application.

FIG. 1 is a functional block diagram of a biological characteristics detection device according to embodiments of the present application. The biological characteristics detection device 100 includes a PPG circuit 103, a light source 108 and N photoelectric converters, wherein the N photoelectric converters are divided into K sets of photoelectric converter sets 110_1~110_K, wherein N and K are integers greater than 1; in the present embodiment, each set of the photoelectric converter sets 110_1~110_K includes N/K photoelectric converters that are parallelly connected, and N/K is an integer greater than 0; however, the present application is not limited thereto, in some embodiments, each set of the photoelectric converter sets 110_1~110_K may include different numbers of photoelectric converters. The PPG circuit 103 is configured to control the light source 108 and N photoelectric converters to sense biological characteristics of an object under test 101, e.g., the blood pressure, blood flow, blood oxygen, cerebral oxygen, muscle oxygen, blood glucose, microcirculatory peripheral vascular pulse rate, respiratory rate, respiratory volume, etc. of a living organism, and periodically generate biological characteristics sampling result $D_R$ according to a pulse repetition cycle $T_{PF}$. In some embodiments, the N photoelectric converters are photodiodes, and the light source 108 is a light-emitting diode (LED); however, the present application is not limited thereto.

The PPG circuit 103 includes a transmitting channel 102, K sets of receiving channels 104_1~104_K and a controller 106, wherein the transmitting channel 102 is configured to perform a light-emission operation EP; the K sets of receiving channels 104_1~104_K are configured to perform a sampling operation SP. When the transmitting channel 102 performs the light-emission operation E, the transmitting channel 102 controls the light source 108 to generate incident light EL onto the object under test 101 which results in a reflective light RL carrying biological characteristics information. The K sets of receiving channels 104_1~104_K correspond to said K sets of photoelectric converter sets 110_1~110_K, when any one receiving channel of the K sets of receiving channels 104_1~104_K performs the sampling operation SP, it controls a corresponding photoelectric converter set of the K sets of photoelectric converter sets 110_1~110_K to sense received light, so as to generate current to the any one receiving channel. The received light includes the reflective light RL with the biological characteristics information; however, light leakage will take place if there is a gap between the biological characteristics detection device 100 and the object under test 101, thereby leading to the received light additionally including ambient light AL.

The controller 106 is configured to control the light source 108 to perform the light-emission operation EP once during each pulse repetition cycle $T_{PF}$, and specifically, during each pulse repetition cycle $T_{PF}$, the controller 106 controls a portion (i.e., during a partial sampling phase; for example, J sets, and J is 1) or all (i.e., during a full sampling phase) of the K sets of photoelectric converter sets 110_1~110_K to perform the sampling operation SP. The transmitting channel 102 includes a light source driver 112, which is configured to drive the light source 108; for example, if the light source 108 is an LED, the light source driver 112 is an LED driver. The receiving channels 104_1~104_K includes current-to-voltage converters 114_1~114_K and are configured to convert the current outputted by the photoelectric converter sets 110_1~110_K into voltage. In some embodiments, the controller 106 is implemented using a digital circuit, and the transmitting channel 102 may further include a digital-to-analog converter 116 coupled between the light source driver 112 and the controller 106; the receiving channels 104_1~104_K may further include an analog-to-digital converter 118_1~118_K coupled between the current-to-voltage converters 114_1~114_K and the controller 106.

With respect to hear rate or cardiac/blood oxygen measurement, the object under test is generally the finger or wrist, and the biological characteristics detection device generally use multiple photoelectric converters corresponding to multiple location, and wherein only one or two locations thereof may provide valid biological characteristics sampling results. The controller 106 of the biological characteristics detection device 100 according to the present application enters the full sampling phase from the partial sampling phase every preset update interval T, so as to re-select J (e.g., one) receiving channels which are most effective for sampling the biological characteristics from the K receiving channels 104_1~104_K corresponding to the K sets of photoelectric converter sets 110_1~110_K as the current receiving channels RXS. The current receiving channels RXS are used during each pulse repetition cycle $T_{PF}$ for simultaneous sampling operation SP, so as to generate biological characteristics sampling result $D_R$ periodically. Since the full sampling phase is carried out once every preset update interval T to compare biological characteristics sampling results $D_R$ sampled by all the receiving channels 104_1~104_K, and if there are other candidates better than the current receiving channels RXS that are currently in use, such better receiving channel(s) will be set as the current receiving channels RXS. In the present application, during each pulse repetition cycle $T_{PF}$, the light source 108 is only driven once; in the present embodiment, the preset update interval T is greater than 1 second, such as 30 seconds, and the length of the pulse repetition cycle $T_{PF}$ is in millisecond level, e.g., several millisecond; therefore, the preset update interval T is much greater than pulse repetition cycle $T_{PF}$.

Figure 2:
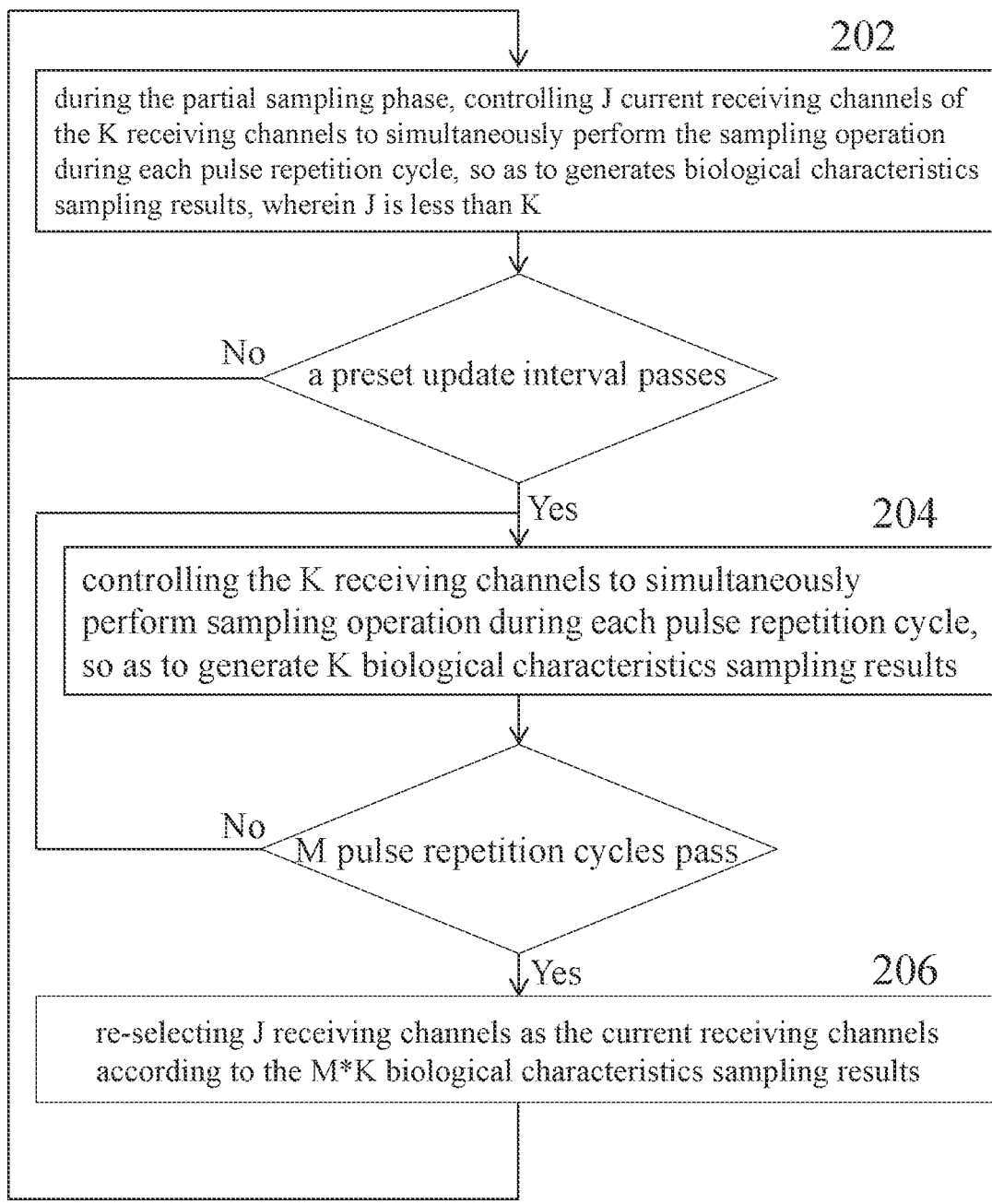
FIG. 2 is flow diagram illustrating the operation procedure of the biological characteristics detection device according to embodiments of the present application.

FIG. 2 is flow diagram illustrating the operation procedure of the biological characteristics detection device according to embodiments of the present application. In Step 202, during the partial sampling phase, the controller 106 controls J current receiving channels RXS of the K receiving channels 104_1~104_K to simultaneously perform the sampling operation SP during each pulse repetition cycle $T_{PF}$, so as to generates J biological characteristics sampling results $D_R$ during each pulse repetition cycle $T_{PF}$. In this phase, the K-J receiving channels other than the current receiving channels RXS will not perform the sampling operation SP; in other words, during each pulse repetition cycle $T_{PF}$, the simultaneous sampling operation SP will only be performed once; in other words, during each pulse repetition cycle $T_{PF}$, the light source 108 will only be irradiated once.

In the present embodiment, when the duration of Step 202 lasts for a preset update interval T, the biological characteristics detection device 100 enters the full sampling phase, i.e., Step 204, in which the controller 106 controls all K receiving channels 104_1~104_K to simultaneously perform sampling operation during each pulse repetition cycle $T_{PF}$, so as to generate K biological characteristics sampling results $D_R$. The full sampling phase will last for M pulse repetition cycles $T_{PF}$, wherein M is an integer greater than 1, so as to collect sufficient biological characteristics sampling results $D_R$ that can be used in Step 206 for determining which J receiving channels from the K receiving channels 104_1~104_K to be selected as the current receiving channels RXS, according to M*K biological characteristics sampling results $D_R$, and then returns to Step 202. It should be noted that, during the M pulse repetition cycles $T_{PF}$ of the full sampling phase, and before the current receiving channels RXS have been determined and updated, the controller 106 still uses the biological characteristics sampling results $D_R$ of the previous current receiving channels RXS.

Specifically, in Step 206, the controller 106 can generate K quality factors FOM corresponding to the K receiving channels 104_1~104_K according to M*K biological characteristics sampling results $D_R$, and determine the current receiving channels RXS according to the K quality factors FOM. In the present application, the quality factor FOM can be any self-defined factors; in one embodiment, the controller 106 generates the K quality factors FOM according to a ratio of the DC component to the AC component of the M*K biological characteristics sampling results $D_R$. In a further embodiment, the controller 106 generates the K quality factors FOM according to the signal intensity of the M*K biological characteristics sampling results $D_R$ at a specific frequency band. In yet another embodiment, the controller 106 further receives a gravity sensing signal G and generates the K quality factors FOM according to the M*K biological characteristics sampling results $D_R$ and the gravity sensing signal G.

Compared with the existing approach where multiple photoelectric converters are sampled alternatively during each pulse repetition cycle $T_{PF}$, thereby driving the light source multiple times during each pulse repetition cycle $T_{PF}$, the biological characteristics detection device 100 according to the present application will only be driven once during each pulse repetition cycle $T_{PF}$; therefore, embodiments of the present application may save more power. Also, compared with another conventional approach where all photoelectric converter are parallelly connected and sampled together, the biological characteristics detection device 100 according to the present application divides all photoelectric converter into multiple sets and increases the number of the receiving channel to correspond to the multiple sets of photoelectric converters; in this way, only the photoelectric converters that are divided into the same set are parallelly connected instead of connecting all the photoelectric converter in parallel, therefore, it poses less impact to the dynamic range specification and suffers less parasitic capacitance effects. Furthermore, even during the M pulse repetition cycles $T_{PF}$ of the full sampling phase, before the current receiving channels RXS are determined and updated, the controller 106 still uses the biological characteristics sampling result $D_R$ from the previous current receiving channels RXS, and hence the measurement of the heart rate and cardiac/blood oxygen level performed by the biological characteristics detection device 100 is not interrupted.

The PPG circuit 103 according to the present application can be implemented using a chip 32, wherein the chip 32 can be a semiconductor chip implemented using various processes, and the N photoelectric converters and the light source 108 are disposed outside the chip 32 where the PPG circuit resides. Yet, the present application is not limited thereto; in some embodiments, the N photoelectric converters and/or the light source 108 can also be disposed in the chip 32 where the PPG circuit resides.

Figure 3:
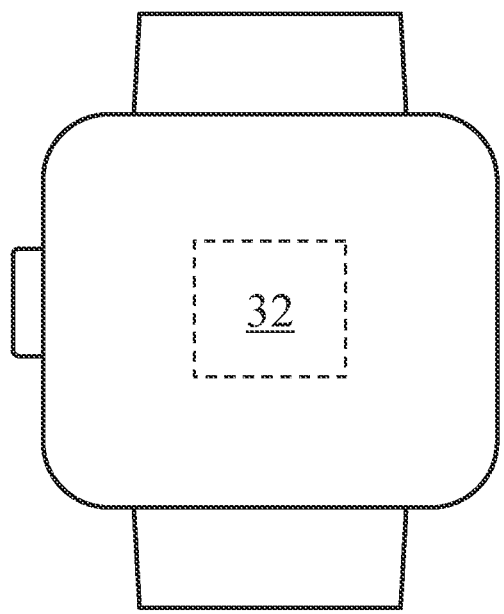
FIG. 3 is a schematic diagram illustrating a chip including the biological characteristics detection device applied in an electronic device according to embodiments of the present application.

FIG. 3 is a schematic diagram illustrating a chip 32 including the biological characteristics detection device 100 according to embodiments of the present application, applied in an electronic device 30. Referring to FIG. 3, the electronic device 30 includes a chip 32. The electronic device 30 may be a wearable electronic device, e.g., watch, necklace or any other smart wearable device. The electronic device 30 may also be a handheld electronic device, such as a smart phone, digital personal assistant, hand-held computing system or tablet computer, etc.

In view of the foregoing, the biological characteristics detection device 100 according to the present application and the related chip 32 and electronic device 30 uses multiple receiving channels, which only increase the overall power consumption slightly but at the same time significantly increase the accuracy of biological characteristics detection devices with multiple photoelectric converters in sensing biological characteristics.

The foregoing only discloses some preferred embodiments of the present application and is not intended to limit the scope of the present application. The present application is subject to various changes and variations to persons having ordinary skill in the art. Any modifications, equivalent substitutions, improvements, etc., made within the spirit and principles of the present disclosure are to be included within the scope of the present application.

What is claimed is:

1. A photoplethysmogram (PPG) circuit, configured to control a light source and N photoelectric converters to sense biological characteristics of an object under test, wherein N is an integer greater than 1, and the PPG circuit comprises:

a transmitting channel, configured to control the light source to perform light emitting operations during pulse repetition cycles;

K receiving channels, wherein K is an integer greater than 1, and the N photoelectric converters are divided into K sets of photoelectric converter sets, the K receiving channels respectively correspond to the K sets of photoelectric converter sets; and a controller, configured to control the PPG circuit to operate in a partial sampling phase or a full sampling phase, when the controller controls the PPG circuit to operate in the partial sampling phase, the controller activates J receiving channels of the K receiving channels as current receiving channels and activates J sets of photoelectric converter sets of the K sets of photoelectric converter sets corresponding to the J receiving channels to sense received light for performing the sampling operation, so as to generate J biological characteristics sampling results during each of the pulse repetition cycles, wherein J is smaller than K; and when the controller controls the PPG circuit to operate in the full sampling phase, the controller activates all receiving channels of the K receiving channels and activates all of the K sets of photoelectric converter sets to sense the received light for performing the sampling operation, so as to generate K biological characteristics sampling results during each of the pulse repetition cycles, and from the K receiving channels, re-select J receiving channels as the current receiving channels to be activated during the next partial sampling phase according to the K biological characteristics sampling results generated during each of the pulse repetition cycles of the full sampling phases, wherein the controller is configured to control the PPG circuit to enter the full sampling phase from the partial sampling phase every preset update interval, so as to periodically generate the J biological characteristics sampling results and the K biological characteristics sampling results, wherein J is 1, and a duration of the full sampling phase comprises M pulse repetition cycles, wherein M is an integer greater than 1, wherein the controller determines the current receiving channels according to M*K biological characteristics sampling results, wherein the controller generates K quality factors corresponding to the K receiving channels according to the M*K biological characteristics sampling results and determines the current receiving channels according to the K quality factors, wherein the controller generates the K quality factors according to a signal intensity of the M*K biological characteristics sampling results at a specific frequency band.

2. The PPG circuit of claim 1, wherein each of the receiving channels corresponds to N/K photoelectric converters, and the N/K photoelectric converters are connected in parallel.

3. The PPG circuit of claim 1, wherein the preset update interval is greater than the pulse repetition cycle.

4. The PPG circuit of claim 1, wherein at periods other than the full sampling phase, the K-J receiving channels other than the current receiving channels of the K receiving channels are free from performing the sampling operation.

5. The PPG circuit of claim 1, wherein the transmitting channel comprises:

a light source driver, configured to drive the light source; and a digital-to-analog converter, coupled between the light source driver and the controller.

6. The PPG circuit of claim 1, wherein the receiving channel comprises:

a current-to-voltage converter, configured to convert current into voltage; and an analog-to-digital converter, coupled between the current-to-voltage converter and the controller.

7. A biological characteristics detection device, comprising:

a PPG circuit, configured to control a single light source and N photoelectric converters to sense biological characteristics of an object under test, wherein N is an integer greater than 1, and the PPG circuit includes:

a transmitting channel, configured to control the single light source to generate an incident light onto the object under test during pulse repetition cycles;

K receiving channels, wherein K is an integer greater than 1, and the N photoelectric converters are divided into K sets of photoelectric converter sets, the K receiving channels respectively correspond to the K sets of photoelectric converter sets; and a controller, configured to control the PPG circuit to operate in a partial sampling phase or a full sampling phase, when the controller controls the PPG circuit to operate in the partial sampling phase, the controller activates J receiving channels of the K receiving channels as current receiving channels and activates J sets of photoelectric converter sets of the K sets of photoelectric converter sets corresponding to the J receiving channels to simultaneously sense a reflective light corresponding to the incident light for performing the sampling operation, so as to generate J biological characteristics sampling results during each of the pulse repetition cycles, wherein J is smaller than K; and when the controller controls the PPG circuit to operate in the full sampling phase, the controller activates all receiving channels of the K receiving channels and activates all of the K sets of photoelectric converter sets to simultaneously sense the reflective light for performing the sampling operation, so as to generate K biological characteristics sampling results during each of the pulse repetition cycles, and from the K receiving channels, re-select J receiving channels as the current receiving channels to be activated during the next partial sampling phase according to the K biological characteristics sampling results generated during each of the pulse repetition cycles of the full sampling phases; and the K sets of photoelectric converter sets, respectively coupled to the K receiving channels, wherein a duration of the full sampling phase comprises M pulse repetition cycles, and M is an integer greater than 1, wherein the controller determines the current receiving channels according to K quality factors corresponding to the K receiving channels, wherein the controller generates the K quality factors according to a signal intensity of M*K biological characteristics sampling results at a specific frequency band.

8. The biological characteristics detection device of claim 7, further comprising:

the light source, coupled to the transmitting channel.

9. A biological characteristics detection method, configured to control a single light source and N photoelectric converters to sense biological characteristics of an object under test, wherein N is an integer greater than 1, the N photoelectric converters are divided into K sets of photoelectric converter sets, and the biological characteristics detection method comprises:

controlling the single light source to perform only one light emitting operation to generate an incident light onto the object under test during each of the pulse repetition cycles;

during a partial sampling phase, only activating J sets of photoelectric converter sets of the K sets of photoelectric converter sets to simultaneously sense a reflective light corresponding to the incident light for performing sampling operation, and generating J biological characteristics sampling results via the activated J sets of photoelectric converter sets during each of the pulse repetition cycles, wherein J is smaller than K;

during a full sampling phase, activating all of the K sets of photoelectric converter sets to simultaneously sense the reflective light for performing the sampling operation, so as to generate K biological characteristics sampling results during each of the pulse repetition cycles, and from the K receiving channels, re-selecting J receiving channels as the current receiving channels to be activated during the next partial sampling phase according to the K biological characteristics sampling results generated during said each of the pulse repetition cycles of the full sampling phases, wherein a duration of the full sampling phase comprises M pulse repetition cycles, and M is an integer greater than 1;

determining the current receiving channels according to K quality factors corresponding to the K receiving channels; and generating the K quality factors according to a signal intensity of M*K biological characteristics sampling results at a specific frequency band.

10. The biological characteristics detection method of claim 9, wherein each of the K sets of photoelectric converter corresponds to N/K photoelectric converters, and the N/K photoelectric converters are connected in parallel.

11. The biological characteristics detection method of claim 9, further comprising:

entering the full sampling phase every preset update interval, and the preset update interval is greater than the pulse repetition cycle.

12. The biological characteristics detection method of claim 9, wherein from the K receiving channels, re-selecting the J receiving channels as the current receiving channels to be activated during the next partial sampling phase according to the K biological characteristics sampling results generated during each of the pulse repetition cycles of the full sampling phase comprises:

from the K sets of photoelectric converter sets, re-selecting the J sets of photoelectric converter sets to be activated during the next partial sampling phase according to the K quality factors.

\* \* \* \* \*